United States Patent
Yang et al.

(10) Patent No.: US 10,584,341 B2
(45) Date of Patent: Mar. 10, 2020

(54) ANTAGONISTIC PDL1 APTAMERS AND THEIR APPLICATIONS IN CANCER THERAPY

(71) Applicants: Academia Sinica, Taipei (TW); National Taiwan University, Taipei (TW)

(72) Inventors: Pan-Chyr Yang, Taipei (TW); Wei-Yun Lai, Taipei (TW); Bo-Tsang Huang, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 0 days.

(21) Appl. No.: 15/755,958

(22) PCT Filed: Aug. 31, 2016

(86) PCT No.: PCT/US2016/049643
§ 371 (c)(1),
(2) Date: Feb. 27, 2018

(87) PCT Pub. No.: WO2017/040620
PCT Pub. Date: Mar. 9, 2017

(65) Prior Publication Data
US 2018/0258431 A1    Sep. 13, 2018

Related U.S. Application Data

(60) Provisional application No. 62/212,772, filed on Sep. 1, 2015.

(51) Int. Cl.
| | |
|---|---|
| *C12N 15/11* | (2006.01) |
| *C12N 15/115* | (2010.01) |
| *A61K 31/711* | (2006.01) |
| *A61P 35/00* | (2006.01) |

(52) U.S. Cl.
CPC ......... *C12N 15/115* (2013.01); *A61K 31/711* (2013.01); *A61P 35/00* (2018.01); *C12N 2310/16* (2013.01); *Y02A 50/463* (2018.01)

(58) Field of Classification Search
None
See application file for complete search history.

(56) References Cited

U.S. PATENT DOCUMENTS

| | | |
|---|---|---|
| 2005/0159351 A1 | 7/2005 | Grate et al. |
| 2011/0097712 A1* | 4/2011 | Cantor ............... C12Q 1/6827 435/6.12 |
| 2011/0251259 A1 | 10/2011 | Defougerolles et al. |
| 2013/0209514 A1 | 8/2013 | Gilboa et al. |

FOREIGN PATENT DOCUMENTS

| | | | |
|---|---|---|---|
| WO | WO 2011/127180 A1 | 10/2011 | |
| WO | WO-2013082448 A1 * | 6/2013 | ........... C12Q 1/6883 |
| WO | WO 2014/197369 A1 | 12/2014 | |

OTHER PUBLICATIONS

PCT/US2016/049643, dated Dec. 21, 2016, International Search Report and Written Opinion.
PCT/US2016/049643, dated Mar. 15, 2018, International Preliminary Report on Patentability.
Prodeus et al., Targeting the PD-1/PD-L1 Immune Evasion Axis With DNA Aptamers as a Novel Therapeutic Strategy for the Treatment of Disseminated Cancers. Mol Ther Nucleic Acids. Apr. 28, 2015;4:e237. doi: 10.1038/mtna.2015.11.
EP 16842876.1, dated Mar. 8, 2019, Extended European Search Report.

* cited by examiner

*Primary Examiner* — Ekaterina Poliakova-Georgantas
(74) *Attorney, Agent, or Firm* — Polsinelli PC

(57) ABSTRACT

Aptamers that bind to and antagonize PDL1 and uses thereof in enhancing immune activity (e.g., promoting T cell proliferation), treating cancer, and/or infectious diseases such as infections caused by enterovirus, HBV, or HCV infection.

23 Claims, 16 Drawing Sheets
Specification includes a Sequence Listing.

SEQUENCE LISTING

```
<160> NUMBER OF SEQ ID NOS: 27

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 1
cgggccacat                                                                10

<210> SEQ ID NO 2
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 2
acgggccaca tcaactcatt gatagacaat gcgtccactg cccgt                         45

<210> SEQ ID NO 3
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 3
cactcaataa ttccactgct acatacgttt                                          30

<210> SEQ ID NO 4
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 4
aaactagggt ccatttgtgt acctgcga                                            28
```

```
<210> SEQ ID NO 5
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 5
acatcaactt gatagacaac tgcgtccact                                30

<210> SEQ ID NO 6
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 6
catctggtac cttacgacgc ttcatctccc                                30

<210> SEQ ID NO 7
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 7
catgttttcg aaagacaatc cgctgccctg                                30

<210> SEQ ID NO 8
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 8
catgttcctt tcgttctgcc ttttccttcc                                30

<210> SEQ ID NO 9
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 9
tccctacggc gctaacacat caacttgata gacaactgcg tccactgcca ccgtgctaca   60
ac                                                                 62

<210> SEQ ID NO 10
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 10
cacatcaact cattgataga caatgcgtcc                                30

<210> SEQ ID NO 11
<211> LENGTH: 62
<212> TYPE: DNA
<213> ORGANISM: Artificial Sequence
```

```
<220> FEATURE:
<223> OTHER INFORMATION: Synthetic polynucleotide

<400> SEQUENCE: 11
tccctacggc gctaaccact caataattcc actgctacat acgtttgcca ccgtgctaca    60
ac                                                                   62

<210> SEQ ID NO 12
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 12
tccctacggc gctaacaaac tagggtccat ttgtgtacct gcgagccacc gtgctacaac    60

<210> SEQ ID NO 13
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 13
tccctacggc gctaaccatc tggtacctta cgacgcttca tctcccgcca ccgtgctaca    60
ac                                                                   62

<210> SEQ ID NO 14
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 14
tccctacggc gctaaccatg ttttcgaaag acaatccgct gccctggcca ccgtgctaca    60
ac                                                                   62

<210> SEQ ID NO 15
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 15
tccctacggc gctaaccatg ttcctttcgt tctgccttttt ccttccgcca ccgtgctaca   60
ac                                                                   62

<210> SEQ ID NO 16
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 16
tccctacggc gctaac                                                    16
```

```
<210> SEQ ID NO 17
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 17
gccaccgtgc tacaac                                                          16

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
gaggaactgg caaaaggatg                                                      20

<210> SEQ ID NO 19
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 19
ttcaagactt caaagagtct gaggta                                               26

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
cttttcctct tgggcatcat                                                      20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
gcatcgtgca ttccttatca                                                      20

<210> SEQ ID NO 22
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 22
gctgccgtca ttttctgc                                                        18

<210> SEQ ID NO 23
<211> LENGTH: 18
<212> TYPE: DNA
<213> ORGANISM: Artificial Sequence
<220> FEATURE:
<223> OTHER INFORMATION: Synthetic polynucleotide
```

```
<400> SEQUENCE: 23
tctcactggc ccgtcatc                                                 18

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
gctgctgaga tgaacaggaa                                               20

<210> SEQ ID NO 25
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 25
ccctgtttga acataaggaa gc                                            22

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
ctaaggccaa ccgtgaaaag                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
accagaggca tacagggaca                                               20
```

ANTAGONISTIC PDL1 APTAMERS AND THEIR APPLICATIONS IN CANCER THERAPY

CROSS-REFERENCE TO RELATED APPLICATIONS

This application is a national stage filing under 35 U.S.C. § 371 of international application PCT/US2016/049643, entitled "ANTAGONISTIC PDL1 APTAMERS AND THEIR APPLICATIONS IN CANCER THERAPY," filed Aug. 31, 2016, which claims the benefit of the filing date under 35 U.S.C. § 119(e) of U.S. Provisional Application No. 62/212,772, entitled "ANTAGONISTIC PDL1 APTAMERS AND THEIR APPLICATIONS IN CANCER THERAPY," filed Sep. 1, 2015. The contents of both are herein incorporated by reference in their entirety.

BACKGROUND OF INVENTION

The immune system is a complex signaling network regulated by several immune checkpoint pathways, which involve co-stimulation and co-inhibition molecules on immune cells that prevent self-reactivity and overly-activated signaling. Programmed cell death-1 protein (PD-1) is a checkpoint molecule, which inhibits T cell activity in peripheral tissues at the time of an inflammatory response to infection, thereby limiting T cell autoimmunity.

PD-1 is mainly expressed on T cells and its expression is induced during T cell activation. Besides T cells, PD-1 is also expressed on other immune cells, such as B cells, dendritic cells, natural killer cells, and macrophages. When bound by one of its ligands such as programmed death-ligand 1 (PDL1), PD-1 inhibits kinases that are involved in T cell activation, such as PI3K and AKT, through the phosphatases SHP1 and SHP2. Moreover, the engagement of PD-1:PDL1 has been shown to inhibit T cell glucose consumption, down-regulate cytokine release, and suppress T cell proliferation.

PDL1 is expressed on antigen-presenting cells (APCs) including B cells, dendritic cells, and macrophages. Moreover, PDL1 expression has been detected on various types of cancer cells, including solid tumors such as non-small-cell lung cancers (NSCLC), melanomas, breast, colon, pancreatic, gastric cancers, and hematologic malignancies such as acute myeloid leukemia, chronic lymphocytic leukemia, and others. Overexpression of PDL1 on cancer cells may lead to tumor immune evasion by increasing PD-1:PDL1 interaction, which dramatically impairs T cell function. Consistently, PDL1 expression is inversely correlated to cancer patient treatment outcomes and overall survival in clinical settings. Hence, new therapeutic agents, such as aptamers, that interfere with the PD-1:PDL1 interaction and antagonize PD-1 intracellular signaling pathways are desired.

Aptamers are short nucleic acid (DNA or RNA) molecules that are capable of forming secondary structures or even complex three-dimensional structures and have specific binding activities to target proteins. Aptamer technology has progressed tremendously since its discovery in the early 1990s. Aptamers have several advantages that make them suitable for therapeutic application, including lower molecular weight, which enables easier penetration through tissue compared to antibodies, low cost of chemical synthesis, established modification methods, and high stability. It is therefore of great interest to develop suitable aptamers having high affinity to a target protein.

SUMMARY OF INVENTION

The present disclosure is based on the development of anti-PDL1 nucleic acid aptamers, which successfully prevented the interaction between PD-1 and PDL1 in vitro and suppressed tumor growth in vivo.

Accordingly, one aspect of the present disclosure features a nucleic acid aptamer that binds PDL1 and neutralizes the inhibitory activity of PDL1 (anti-PDL1 aptamer). Any of the nucleic acid aptamers of the present disclosure may be 30-62 nucleotides (nts) in length.

In some embodiments, the nucleic acid aptamer comprises a nucleic acid motif having the nucleotide sequence of 5'-CGGGCCACAT-3' (SEQ ID NO:1). Such an anti-PDL1 aptamer may comprise a nucleic acid sequence that is at least 85% (e.g., at least 90%, at least 95% or above) identical to ACGGGCCACATCAACTCATTGATAGACAATGCGTCCACTGCCCGT (SEQ ID NO: 2). In one example, the nucleic acid aptamer comprises the nucleic acid sequence of SEQ ID NO:2. In another example, the nucleic acid aptamer consists of the nucleic acid sequence of SEQ ID NO:2.

In other embodiments, the nucleic acid aptamer may comprise a nucleic acid sequence that is at least 85% (e.g., at least 90%, at least 95% or above) identical to (i)
(SEQ ID NO: 2)
ACGGGCCACATCAACTCATTGATAGA CAATGCGTCCACTGCCCGT (ii)
(SEQ ID NO: 3)
CACTCAATAATTCCACTGCTACATACGTTT;

(iii)
(SEQ ID NO: 4)
AAACTAGGGTCCATTTGTGTACCTGCGA;

(iv)
(SEQ ID NO: 5)
ACATCAACTTGATAGACAACTGCGTCCACT;

(v)
(SEQ ID NO: 6)
CATCTGGTACCTTACGACGCTTCATCTCCC;

(vi)
(SEQ ID NO: 7)
CATGTTTTCGAAAGACAATCCGCTGCCCTG;
or (vii)
(SEQ ID NO: 8)
CATGTTCCTTTCGTTCTGCCTTTTCCTTCC.

In some embodiments, the nucleic acid aptamer comprises a nucleic acid sequence of any one of SEQ ID NOs: 2-8. In other embodiments, the nucleic acid aptamer consists a nucleic acid sequence of any one of SEQ ID NOs:2-8.

Another aspect of the present disclosure features a pharmaceutical composition, comprising any of the anti-PDL1 aptamers described herein and a pharmaceutically acceptable carrier.

In yet another aspect, the present disclosure provides a method for treating cancer (e.g., melanoma, non-small cell lung cancer, colorectal cancer, or renal-cell cancer), comprising administering to a subject in need of the treatment an effective amount of any of the pharmaceutical compositions described herein. In some embodiments, the subject may be a human patient having, suspected of having, or at risk for a cancer, such as those described herein.

In another aspect, the present disclosure provides a method for treating an infectious disease, comprising administering to a subject in need thereof an effective amount of any of the pharmaceutical compositions described herein. In some embodiments, the subject may be a human patient having or suspected of having infection (e.g., an infection caused by enterovirus, HBV, HCV, HAV, HDV, or HEV).

Further, the present disclosure provides a method of enhancing immune activity in a subject in need of the treatment, the method comprising administering to a subject in need thereof an effective amount (e.g., effective in increasing T cell activation) of any of the anti-PDL1 aptamer-containing pharmaceutical compositions as described herein.

Also within the scope of the present disclosure are (a) pharmaceutical compositions for use in treating cancer (e.g., lung cancer, melanoma, colorectal cancer, or renal-cell cancer), or an infectious disease such as enterovirus, HBV, HCV, HAV, HDV, or HEV infection, wherein the pharmaceutical composition comprises any of the anti-PDL1 aptamers as described herein, and a pharmaceutically acceptable carrier; and (b) uses of the anti-PDL1 aptamer for manufacturing a medicament for treating cancer such as those described herein, or an infectious disease such as those described herein.

The details of one or more embodiments of the invention are set forth in the description below. Other features or advantages of the present invention will be apparent from the following drawings and detailed description of several embodiments, and also from the appended claims.

DETAILED DESCRIPTION OF INVENTION

PDL1, the ligand of immune inhibitory receptor PD-1, is expressed on many solid tumors. The engagement of PDL1:

PD-1 triggers immunosuppressive pathways and impairs anti-tumor activities of immune cells. The antagonistic PDL1 aptamers, provided herein, can block interaction between PDL1 and PD-1 and induce anti-tumor activities of immune cells.

A large proportion of targeted therapeutic agents against PDL1 are monoclonal antibodies. Compared to antibodies and other traditional protein-based drugs, the nucleic acid-based PDL1-targeting aptamers, provided herein, have higher stability and lower cost for large scale synthesis. Moreover, the PDL1 aptamers are amenable to chemical modification to enhance bioavailability and stability with little batch effect.

Figure 5:
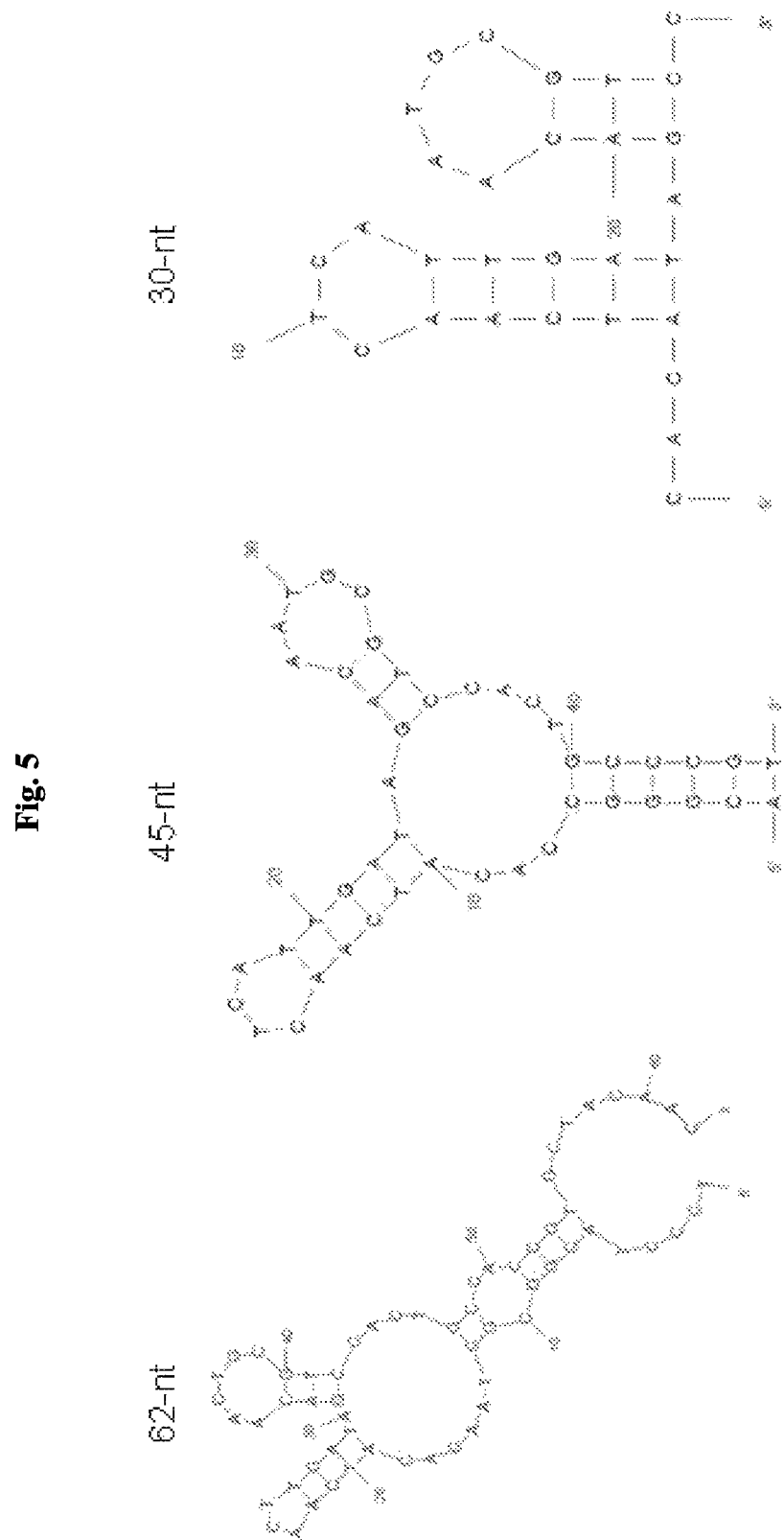
FIG. 5 includes diagrams showing the sequence and secondary structure of a 62-nt (left panel, SEQ ID NO: 9), a 45-nt (middle panel, SEQ ID NO: 2), and a 30-nt (right panel, SEQ ID NO: 10) anti-PDL1 aptamer. The secondary structure of each aptamer was predicted using Mfold.

Aptamers as described herein can be nucleic acid molecules (e.g., single-stranded DNA or RNA), which may form specific secondary and tertiary structures at physiologic conditions. An exemplary PDL1 antagonist aptamer (aptPDL1), described herein, is a 45-nucleotide long DNA oligonucleotide which forms two stem-loop structures by Mfold prediction. FIG. 5. The dissociation constant of aptPDL1 toward PDL1 was approximately 5 nM, indicating that aptPDL1 binds to PDL1 with much higher affinity than PD1 protein (dissociation constant of 770 nM to PDL1). aptPDL1 was shown to efficiently prevent PD-1 from binding PDL1 in in vitro using a competition assay. The 50% effective dose ($ED_{50}$) of aptPDL1 that blocked PD-1:PDL1 interaction was approximately 12 nM. In a syngeneic mice model, intratumoral and intraperitoneal injection of aptPDL1 significantly suppressed the growth of PDL1-expressing CT26 colorectal tumors. Furthermore, successive doses of intraperitoneally administered aptPDL1 led to significant tumor suppressive effects in a LL/2 murine syngeneic tumor model.

The results provided herein indicate that anti-PDL1 aptamers, such as aptPDL1, are promising surrogates for PDL1 antagonistic monoclonal antibodies. Nucleic acid-based therapeutic agents, such as anti-PDL1 aptamers (e.g., aptPDL1) have advantages in synthesis, stability, and patient tolerance. Aptamers can readily be synthesized by chemical reactions that have lower costs, lower batch effects, and higher purity as compared to antibody synthesis. Aptamers can be preserved in a powder form without loss of drug efficacy and stability. Furthermore, nucleic acid-based therapeutic agents (e.g., DNA-based or RNA-based therapeutic agents) have shown little toxicity and low immunogenicity in animal studies and preclinical trials.

Anti-PDL1 aptamers such as aptPDL1 may target the PDL1 extracellular domain on cell surfaces. Such aptamer molecules would have higher target accessibility as compared to small chemical drugs that target intracellular SHP1 and SHP2 phosphatase domains or siRNAs which degrade PDL1 mRNA. In addition, anti-PDL1 aptamers can be easily modified to increase affinity and specificity to PDL1, resist degradation against endo- or exo-nucleases in the blood stream, and prolong serum half-life in the circulation system. Suitable modifications of nucleic acid-based molecules to achieve one or more of such purposes are known in the art or disclosed herein. For example, feasible modifications of anti-PDL1 aptamers such as aptPDL1 may include introducing functional groups at the 5'- or 3'-end of an anti-PDL1 aptamer, introducing modified bases into the nucleotide sequence, and/or modify linkage bonds between adjacent nucleotides.

Accordingly, the present disclosure is based on the development of a number of anti-PDL1 nucleic acid aptamers and the successful inhibition of the PD-1/PDL1 interaction by exemplary anti-PDL1 aptamers. As disclosed herein, the anti-PDL1 aptamer (e.g., aptPDL1) markedly reduced tumor growth when administered intratumorally or intraperitoneally in mice inoculated with CT26 colorectal cancer cells or LL/2 lung carcinoma cells. Thus, anti-PDL1 aptamers such as those described herein would be effective in enhancing immune activity and preventing tumor growth, thereby providing effective treatments for cancer. Such anti-PDL1 aptamers would also be effective in inhibiting infection and thus be benefit in treating infectious diseases (e.g., enterovirus or HBV infection).

Accordingly, described herein are anti-PDL1 aptamers, pharmaceutical compositions comprising such, and methods for enhancing immune activity and/or treating diseases such as cancer and infectious diseases with the anti-PDL1 aptamers disclosed herein.

Anti-PDL1 Aptamers

Described herein are nucleic acid aptamers that bind to PDL1 and inhibits it activity (anti-PDL1 aptamers), thereby enhancing immune activity such as T cell activity. Accordingly, the anti-PDL1 aptamers disclosed herein would benefit treatment of cancer and infectious diseases.

A nucleic acid aptamer as used herein refers to a nucleic acid molecule (DNA or RNA) having a binding activity for a particular target molecule (e.g., PDL1). The aptamer can bind to a particular target molecule and thereby inhibit the activity of the target molecule, via, e.g., blocking the binding of the target molecule to a cognate ligand, causing conformational changes of the target molecule, and/or blocking the activity center of the target molecule. The anti-PDL1 aptamer of the present disclosure, in linear or circular form, may be an RNA, a DNA (e.g., a single-stranded DNA), a modified nucleic acid, or a mixture thereof. The anti-PDL1 aptamers may be non-naturally molecules (e.g., containing a nucleotide sequence not existing in native genes or containing modified nucleotides not existing in nature). Alternatively or in addition, the anti-PDL1 aptamers may not contain a nucleotide sequence that encodes a functional peptide.

PDL1, referring to programmed death-ligand 1 protein (also known as CD274 or B7-H1), is a cell surface protein that plays a major role in suppressing the immune system, for example, during pregnancy, tissue allografts, autoimmune diseases, infections and cancer. PDL1 binds to its receptor, PD-1, which is expressed on activated T cells, B cells and myeloid cells, to modulate activation or inhibition. In humans, PDL1 is encoded by the CD274 gene. An exemplary amino acid sequence of human PDL1 can be found under GenBank accession number NP_001254635.

The anti-PDL1 nucleic acid aptamer disclosed herein may comprise a nucleic acid motif having the nucleotide sequence of '5-CGGGCCACAT-3' (SEQ ID NO:1). The motif of SEQ ID NO:1 is expected to the be the key domain responsible for interacting with PDL1 and blocking its interaction with PD-1. Accordingly, nucleic acid molecules comprising this motif is expected to be an anti-PDL1 aptamer as described herein. The anti-PDL1 nucleic acid aptamer comprising the motif of SEQ ID NO:1 may comprise a nucleotide sequence at least 85% (e.g., 90%, 95%, or 98%) identical to ACGGGCCACATCAACTCATTGATAGACAATGCGTCCACTGCCCGT (SEQ ID NO: 2), in which the motif of SEQ ID NO:1 is underlined. The up to 15% variations can occur at any residues outside the motif of SEQ ID NO:1. In some embodiments, the anti-PDL1 nucleic acid aptamer may comprise the nucleotide sequence of SEQ ID NO:2. In some embodiments, the anti-PDL1 nucleic acid aptamer consists of SEQ ID NO:2.

In other examples, the anti-PDL1 nucleic acid aptamer disclosed herein may comprise a nucleotide sequence at least 85% (e.g., 90%, 95%, or 98%) identical to (SEQ ID NO: 2)
ACGGGCCACATCAACTCATTGATAGACAATGCGTCCACTGCCCGT, (SEQ ID NO: 3)
CACTCAATAATTCCACTGCTACATACGTTT, (SEQ ID NO: 4)
AAACTAGGGTCCATTTGTGTACCTGCGA, (SEQ ID NO: 5)
ACATCAACTTGATAGACAACTGCGTCCACT, (SEQ ID NO: 6)
CATCTGGTACCTTACGACGCTTCATCTCCC, (SEQ ID NO: 7)
CATGTTTTCGAAAGACAATCCGCTGCCCTG,
or (SEQ ID NO: 8)
CATGTTCCTTTCGTTCTGCCTTTTCCTTCC.

Such anti-PDL1 nucleic acid aptamer disclosed herein may comprise or consist of the nucleotide sequence of (SEQ ID NO: 2)
ACGGGCCACATCAACTCATTGATAGACAATGCGTCCACTGCCCGT, (SEQ ID NO: 3)
CACTCAATAATTCCACTGCTACATACGTTT, (SEQ ID NO: 4)
AAACTAGGGTCCATTTGTGTACCTGCGA, (SEQ ID NO: 5)
ACATCAACTTGATAGACAACTGCGTCCACT, (SEQ ID NO: 6)
CATCTGGTACCTTACGACGCTTCATCTCCC, (SEQ ID NO: 7)
CATGTTTTCGAAAGACAATCCGCTGCCCTG,
or (SEQ ID NO: 8)
CATGTTCCTTTCGTTCTGCCTTTTCCTTCC.

The "percent identity" of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, word-length-12 to obtain nucleotide sequences homologous to the nucleic acid molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other embodiments, the anti-PDL1 aptamers described herein may contain up to 8 (e.g., up to 7, 6, 5, 4, 3, 2, or 1) nucleotide variations as compared with a reference sequence, such as any one of SEQ ID NOs:1-8. Positions where such variations can be introduced can be determined based on, e.g., the secondary structures of the aptamers which may be predicted using a computer algorithm, such as Mfold. As an example, positions where such variations can be introduced can be determined based on the secondary structure of TCCCTACGGCGCTAACACATCAACTT-GATAGACAACTGCGTCCACTGCCACCGTGCTACA-AC (SEQ ID NO: 9), ACGGGCCACATCAACTCATTGA-TAGACAATGCGTCCACTGCCCGT (SEQ ID NO: 2), or CACATCAACTCATTGATAGACAATGCGTCC (SEQ ID NO: 10), as shown in FIG. 5. For example, a base pair in a double-strand stem region may be mutated to a different base pair. Such mutations would maintain the base pair in the double-strand region at that position and thus would have no significant impact on the overall secondary structure of the aptamer. This type of mutations is well known to those skilled in the art. For example, an A-T pair may be mutated to a T-A pair. Alternatively, it may be mutated to a G-C or a C-G pair. In another example, a G-C pair may be mutated to a C-G pair. Alternatively, it may be mutated to an A-T pair or a T-A pair.

Any of the anti-PDL1 aptamers disclosed herein may contain about 30-80 nucleotides (nts) in length. In some embodiments, the nucleic acid aptamer comprising a nucleic acid motif is about 40-80 nts, 40-65 nts, 40-62 nts, 50-80 nts, 60-80 nts, or 70-80 nts. In some embodiments, the nucleic acid aptamer comprising a nucleic acid motif is about 30-70 nts, 30-65 nts, 30-62 nts, 30-60 nts, 30-50 nts, or 30-40 nts. In some specific examples, the length of the anti-PDL1 aptamers may range from about 50 nts to about 60 nts.

In general, the terms "about" and "approximately" mean within an acceptable error range for the particular value as determined by one of ordinary skill in the art. "About" can mean a range of less than ±30%, preferably less than ±20%, more preferably less than ±10%, more preferably less than ±5%, and more preferably still less than ±1% of a given value.

In some embodiments, the anti-PDL1 aptamers described herein may bind to PDL1 (e.g., human PDL1) with a dissociation constant (Kd) lower than 20 nM (e.g., 15 nM, 10 nM, 5 nm, 1 nm, or less). The anti-PDL1 aptamer may specifically bind human PDL1. Alternatively, the aptamer may bind to PDL1 molecules from different species (e.g., human and mouse). When binding to a PDL1 molecule expressed on the cell surface, such an aptamer may inhibit the activity of PDL1 (thus increasing T cell activity) by at least 20% (e.g., 40%, 50%, 80%, 100%, 2-fold, 5-fold, 10-fold, 100-fold, or 1,000-fold). The inhibitory activity of an anti-PDL1 aptamer on PDL1 (and thus the activation in enhancing T cell activity) may be determined by methods known in the art, e.g., T cell proliferation assays, which have been described previously, such as in Clay T. M., et al., Assays for Monitoring Cellular Immune Responses to Active Immunotherapy of Cancer, *Clin Cancer Res.*, May 2001, 7, 1127; the relevant teachings of which are incorporated by reference herein. It should be appreciated that the methods for measuring T cell activity provided herein are exemplary and are not meant to be limiting.

Provided below are a number of exemplary anti-PDL1 aptamers:

aptPDL1:
(SEQ ID NO: 2)
ACGGGCCACATCAACTCATTGATAGACAATGCGTCCACTGCCCGT

AP14:
(SEQ ID NO: 11)
TCCCTACGGCGCTAACCACTCAATAATTCCACTGCTACATACGTTT*GCCA*

*CCGTGCTACAAC*

-continued

AP22:
(SEQ ID NO: 12)
TCCCTACGGCGCTAACAAACTAGGGTCCATTTGTGTACCTGCGAGCCACC

GTGCTACAAC

AP32:
(SEQ ID NO: 9)
TCCCTACGGCGCTAACACATCAACTTGATAGACAACTGCGTCCACTGCCA

CCGTGCTACAAC

AP33:
(SEQ ID NO: 13)
TCCCTACGGCGCTAACCATCTGGTACCTTACGACGCTTCATCTCCCGCCA

CCGTGCTACAAC

AP36:
(SEQ ID NO: 14)
TCCCTACGGCGCTAACCATGTTTTCGAAAGACAATCCGCTGCCCTGGCCA

CCGTGCTACAAC

AP48:
(SEQ ID NO: 15)
TCCCTACGGCGCTAACCATGTTCCTTTCGTTCTGCCTTTTCCTTCCGCCA

CCGTGCTACAAC

In the above noted exemplary anti-PDL1 aptamers, the 5'- and 3'-end italicized regions are the 5' and 3' primer regions (see Example 1 below), which can be replaced or modified with no significant impact on the PDL1 binding activity of these aptamers.

In some embodiments, any of the anti-PDL1 aptamers described herein may contain non-naturally-occurring nucleobases, sugars, or covalent internucleoside linkages (backbones). Such a modified oligonucleotide confers desirable properties, for example, enhanced cellular uptake, improved affinity to the target nucleic acid, and increased in vivo stability.

In one example, the aptamer described herein has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the aptamers described herein include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted C1 to C10 alkyl or C2 to C10 alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

Alternatively or in addition, aptamers described herein include one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of aptamer molecules to their targeting sites. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Alternatively or in addition, the anti-PDL1 aptamers as described herein may comprise one or more locked nucleic acids (LNAs). An LNA, often referred to as inaccessible RNA, is a modified RNA nucleotide, in which the ribose moiety is modified with an extra bridge connecting the 2' oxygen and 4' carbon. This bridge "locks" the ribose in the 3'-endo (North) conformation, which is often found in the A-form duplexes. LNA nucleotides can be used in any of the anti-PDL1 aptamers described herein. In some examples, up to 50% (e.g., 40%, 30%, 20%, or 10%) of the nucleotides in an anti-PDL1 aptamer are LNAs. In some examples, an anti-PDL1 aptamer may comprise 10, 8, 6, 5, 4, 3, 2, or 1 LNA.

Any of the aptamers described herein can be prepared by conventional methods, e.g., chemical synthesis or in vitro transcription. Their intended bioactivity as described herein can be verified by, e.g., those described in the Examples below. Vectors for expressing any of the anti-PDL1 aptamers are also within the scope of the present disclosure.

Any of the aptamers described herein may be conjugated to one or more polyether moieties, such as polyethylene glycol (PEG) moieties, via covalent linkage, non-covalent linkage, or both. Accordingly, in some embodiments, aptamers described herein are PEGylated. The disclosure is not meant to be limiting with respect to a PEG moiety of a specific molecular weight. In some embodiments, the polyethylene glycol moiety has a molecular weight ranging from 5 kDa to 100 kDa, 10 kDa to 80 kDa, 20 kDa to 70 kDa, 20 kDa to 60 kDa, 20 kDa to 50 kDa, or 30 kDa to 50 kDa. In some examples, the PEG moiety has a molecular weight of 40 kDa. The PEG moiety conjugated to the anti-PDL1 aptamer described herein can be linear or branched. It may be conjugated to the 5' end of the nucleic acid aptamer, the 3' end of the aptamer, or both. When needed, the PEG moiety can be conjugated to the 3' end of the nucleic acid aptamer covalently.

Methods for conjugating PEG moieties to nucleic acids are known in the art and have been described previously, for example, in PCT Publication No. WO 2009/073820, the relevant teachings of which are incorporated by reference herein. It should be appreciated that the PEG conjugated nucleic acid aptamers and methods for conjugating PEG to the nucleic acid aptamers described herein, are exemplary and not meant to be limiting.

Pharmaceutical Compositions

One or more of the anti-PDL1 aptamers, or PEG conjugates thereof as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

In some examples, the pharmaceutical composition described herein comprises liposomes containing the PDL1 binding aptamers (or a vector for producing the aptamer), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-PDL1 aptamers as described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the PDL1 binding aptamer, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic PDL1 binding aptamer compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets having a suitable size and can have a pH in the range of 5.5 to 8.0.

The emulsion compositions can be those prepared by mixing an anti-PDL1 aptamer with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Methods of Treatment

Any of the anti-PDL1 aptamers, or PEG conjugates thereof as described herein can be used to enhance immune activity, particularly promoting T cell proliferation, thereby effective in treating cancer, or infectious diseases such as viral (e.g., enterovirus, HBV, HCV, HAV, HDV, or HEV) infection or bacterial infection.

To practice the method disclosed herein, an effective amount of the pharmaceutical composition described herein that contains at least one anti-PDL1 aptamer can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-PDL1 aptamer-containing composition as described herein can be aerosolized using a fluorocarbon formulation and a metered dose inhaler, or inhaled as a lyophilized and milled powder.

As used herein, "an effective amount" refers to the amount of each active agent required to confer therapeutic effect on the subject, either alone or in combination with one or more other active agents. In some embodiments, the therapeutic effect is reduced tumor burden, reduction of cancer cells, or increased immune activity. Determination of whether an amount of the PDL1 binding aptamers achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a PDL1 binding aptamer may be appropriate. Various formulations and devices for achieving sustained release are known in the art.

In one example, dosages for an anti-PDL1 aptamer as described herein may be determined empirically in individuals who have been given one or more administration(s) of the PDL1 binding aptamer. Individuals are given incremental dosages of the antagonist. To assess efficacy of the antagonist, an indicator of the disease/disorder can be followed.

Generally, for administration of any of the anti-PDL1 aptamers described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the PDL1 binding aptamer, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the PDL1 binding aptamer used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a PDL1 binding aptamer as described herein will depend on the specific PDL1 binding aptamer, the type and severity of the disease/disorder, whether the PDL1 binding aptamer is administered for preventive or therapeutic purposes, previous therapy, the patient's clinical history and response to the antagonist, and the discretion of the attending physician. A clinician may administer a PDL1 binding aptamer, until a dosage is reached that achieves the desired result. In some embodiments, the desired result is a decrease in tumor burden, a decrease in cancer cells, or increased immune activity. Methods of determining whether a dosage resulted in the desired result would be evident to one of skill in the art. Administration of one or more PDL1 binding aptamers can be continuous or intermittent, depending, for example, upon the recipient's physiological condition, whether the purpose of the administration is therapeutic or prophylactic, and other factors known to skilled practitioners. The administration of a PDL1 binding aptamer may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the PDL1 binding aptamers described herein are administered to a subject in need of the treatment at an amount sufficient to reduce tumor burden or cancer cell growth, by at least 5% (e.g., 10%, 20%, 30%, 40%, 50%, 60%, 70%, 80%, 90% or greater) in vivo. In other embodiments, the PDL1 binding aptamers are administered in an amount effective in reducing the activity level of PDL1 by at least 5% (e.g., 10%, 20%, 30%, 40%, 50%, 60%, 70%, 80%, 90% or greater). In other embodiments, the PDL1 binding aptamers are administered in an amount effective in increasing immune activity by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble PDL1 binding aptamers can be administered by the drip method, whereby a pharmaceutical formulation containing the PDL1 binding aptamer and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the PDL1 binding aptamer, can be dissolved and administered in a pharmaceutical excipient such as Water-for-Injection, 0.9% saline, or 5% glucose solution.

In one embodiment, a PDL1 binding aptamer is administered via site-specific or targeted local delivery techniques. Examples of site-specific or targeted local delivery techniques include various implantable depot sources of the PDL1 binding aptamer or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994)

269:542; Zenke et al., Proc. Natl. Acad. Sci. USA (1990) 87:3655; Wu et al., J. Biol. Chem. (1991) 266:338.

Therapeutic compositions containing a polynucleotide (e.g., the PDL1 binding aptamers described herein or vectors for producing such) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The subject to be treated by the methods described herein can be a mammal, such as a farm animals, sport animals, pets, primates, horses, dogs, cats, mice and rats. In one example, the subject is a human. The anti-PDL1 aptamer-containing composition may be used for enhancing immune activity, for example, T cell activity, in a subject in need of the treatment. In some examples, the subject may be a human patient having, suspected of having, or at risk for a cancer, such as lung cancer, melanoma, colorectal cancer, or renal-cell cancer. In other examples, the subject can be a human patient having or suspected of having enterovirus, HBV, HCV, HAV, HDV, or HEV infection. Such a patient can also be identified by routine medical practices.

A subject having a target disease or disorder (e.g., cancer, viral infection such as HBV infection, or bacterial infection) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

The particular dosage regimen, i.e., dose, timing and repetition, used in the method described herein will depend on the particular subject (e.g., a human patient) and that subject's medical history.

In some embodiments, the anti-PDL1 aptamer may be co-used with another suitable therapeutic agent (e.g., an anti-cancer agent an anti-viral agent, or an anti-bacterial agent). Alternatively or in addition, the anti-PDL1 aptamer may also be used in conjunction with other agents that serve to enhance and/or complement the effectiveness of the agents.

Treatment efficacy for a target disease/disorder can be assessed by, e.g., a method described in the Examples below.

Kits for Use in Alleviating a Target Disease

The present disclosure also provides kits for use in enhancing immune activity (e.g., T cell activity), alleviating cancer (e.g., lung cancer, melanoma, colorectal cancer, or renal-cell cancer), and/or treating or reducing the risk for enterovirus, HBV, HCV, HAV, HDV, or HEV infection. Such kits can include one or more containers comprising an aptamer that binds PDL1, e.g., any of those described herein.

In some embodiments, the kit can comprise instructions for use in accordance with any of the methods described herein. The included instructions can comprise a description of administration of the aptamer to treat, delay the onset, or alleviate a target disease as those described herein. The kit may further comprise a description of selecting an individual suitable for treatment based on identifying whether that individual has the target disease. In still other embodiments, the instructions comprise a description of administering the aptamer to an individual at risk of the target disease.

The instructions relating to the use of a PDL1 binding aptamer generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with cancer, such as those described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PDL1 binding aptamer as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE 1

Identification of Human PDL1 Targeting Aptamers by Nitrocellulose Filter SELEX

Figure 1:
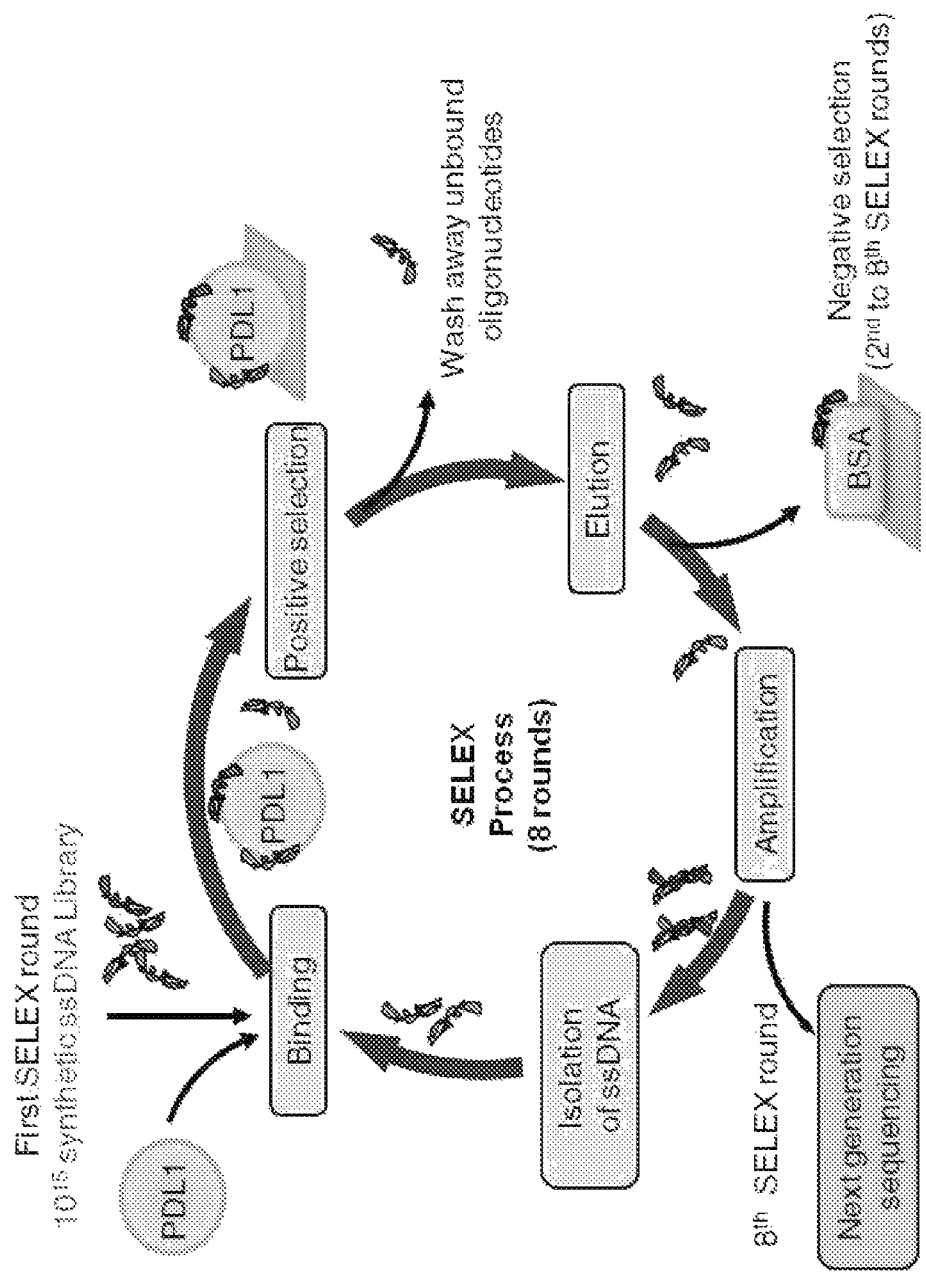
FIG. 1 is a schematic illustration showing the process of selecting nucleic acid aptamers binding to PDL1 via SELEX. In this exemplary schematic, the nitrocellulose filter SELEX process for screening human PDL1-targeting aptamers is shown.

Human PDL1 targeting aptamer was identified based on nitrocellulose filter SELEX (FIG. 1). The synthetic single strand DNA library was composed of single strand DNAs having 62-nucleotides comprising thirty random nucleotides ($[N]_{30}$N=A, T, G, C) flanked by a primer sequence of TCCCTACGGCGCTAAC (SEQ ID NO: 16) that is 5' to the random nucleotides and a primer sequence of GCCACCGTGCTACAAC (SEQ ID NO: 17) that is 3' to the random nucleotides. In the first round of SELEX, $10^{15}$ molecules of ssDNA library were incubated with recombinant human PDL1 protein. Then, ssDNAs which bound to PDL1 protein were collected by nitrocellulose filter and unbound ssDNAs were removed through repetitive washing. The PDL1-bound ssDNAs were eluted by heating and amplified by PCR with biotin-labeled forward primers. ssDNAs were isolated through streptavidin beads and subjected to next round of selection. From the second to the eighth round of selection, bovine serum albumin (BSA) was used for negative selection. In brief, eluted ssDNAs which bound to PDL1 protein were incubated with BSA and then passed through nitrocellulose filter. Flow-through was collected and amplified by PCR. After eight rounds of selection, PDL1-bound ssDNAs were subjected to next-generation sequencing.

EXAMPLE 2

Figure 2:
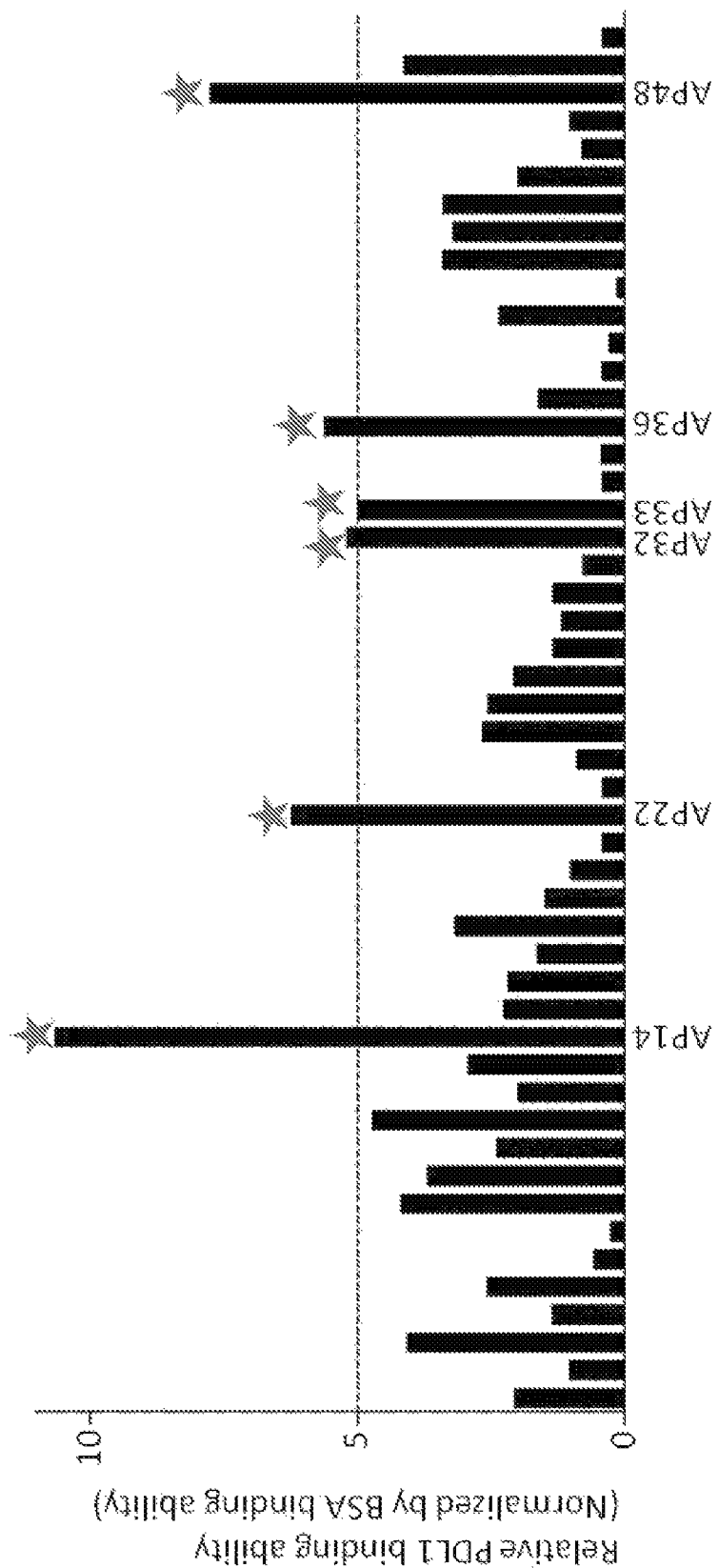
FIG. 2 is a chart showing the relative binding ability of candidate aptamers toward PDL1, including AP14, AP22, AP32, AP33, AP 36, and AP 48.

Evaluation of the Relative Binding Ability of Candidate PDL1 Aptamers Using Nitrocellulose Filter Binding Assay The sequences of candidate PDL1 targeting aptamers were ranked by output reads from next-generation sequencing and sequences with output reads over 100 were analyzed. Among them, top 50 candidate aptamer sequences accounted for over 85% output reads. To evaluate their binding abilities toward PDL1, these top 50 candidate aptamers were synthesized and analyzed by nitrocellulose filter binding assay. The binding abilities toward BSA were used as negative control. In brief, candidate aptamer was incubated with PDL1 or BSA, respectively. Aptamer-protein complexes were collected by nitrocellulose filter and eluted by heating. The number of eluted aptamer was quantified by quantitative PCR and normalized by dividing the signal from PDL1 group to signal from BSA group. In order to find out the PDL1 aptamer with higher specificity, the cut-off value was set at 5. The results revealed that six candidate PDL1 aptamers were passed this criterion including AP14, AP22, AP32, AP33, AP36, AP48 (FIG. 2).

EXAMPLE 3

Figure 3:
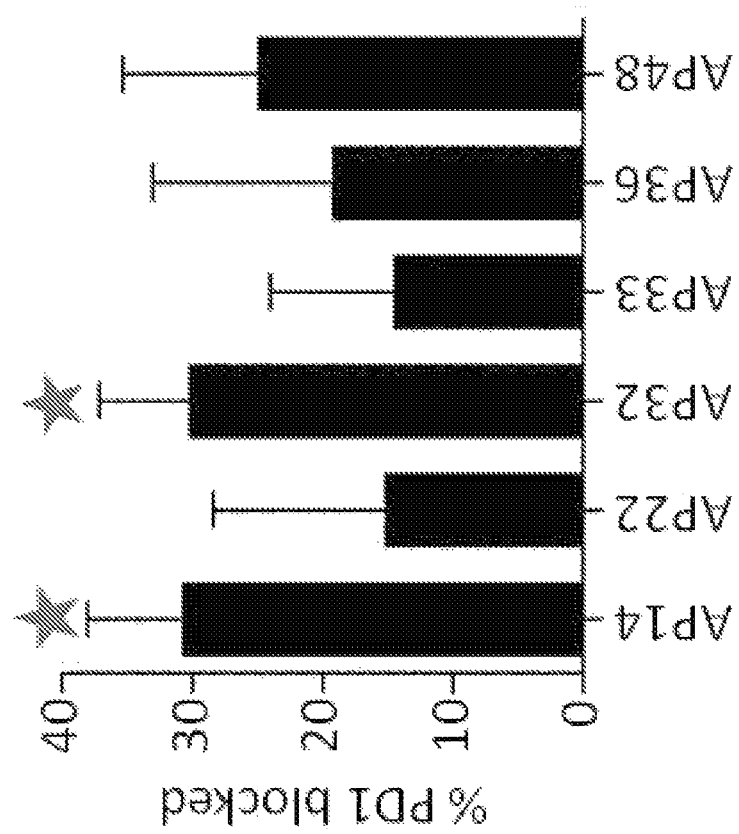
FIG. 3 is a chart depicting the efficacy of candidate PDL1 aptamers for blocking the interaction between PDL1 and PD-1 in a competition assay.

Identification of Antagonistic PDL1 Aptamers Using an ELISA-Based Competition Assay To investigate the efficacy of candidate PDL1 aptamers as antagonistic agents, ELISA-based competition assay was performed. Human PDL1 recombinant protein (2 µg/ml) was coated onto wells of 96-well ELISA plates and blocked by BSA (10 mg/ml). Human PD-1 protein (0.6 µg/ml) and aptamer (500 nmole/l) were added into wells simultaneously. After washing away unbound human PD-1 protein, PD-1 protein which remained in wells was detected by HRP-labeled anti-human IgG antibody. TMB was used as HRP substrate for color development and absorbance at 652 nm was detected by ELISA plate reader. Remained human PD-1 protein amount was quantified using standard curve which built by serial diluted human PD-1 protein. Wells without PDL1 coating were used as negative control. The results showed that six candidate PDL1 aptamers blocked from 12% to 30% of PD-1:PDL1 interaction (FIG. 3). Among them, AP14 and AP32 revealed the highest potency as PDL1 blocking antagonistic aptamers.

Figure 4:
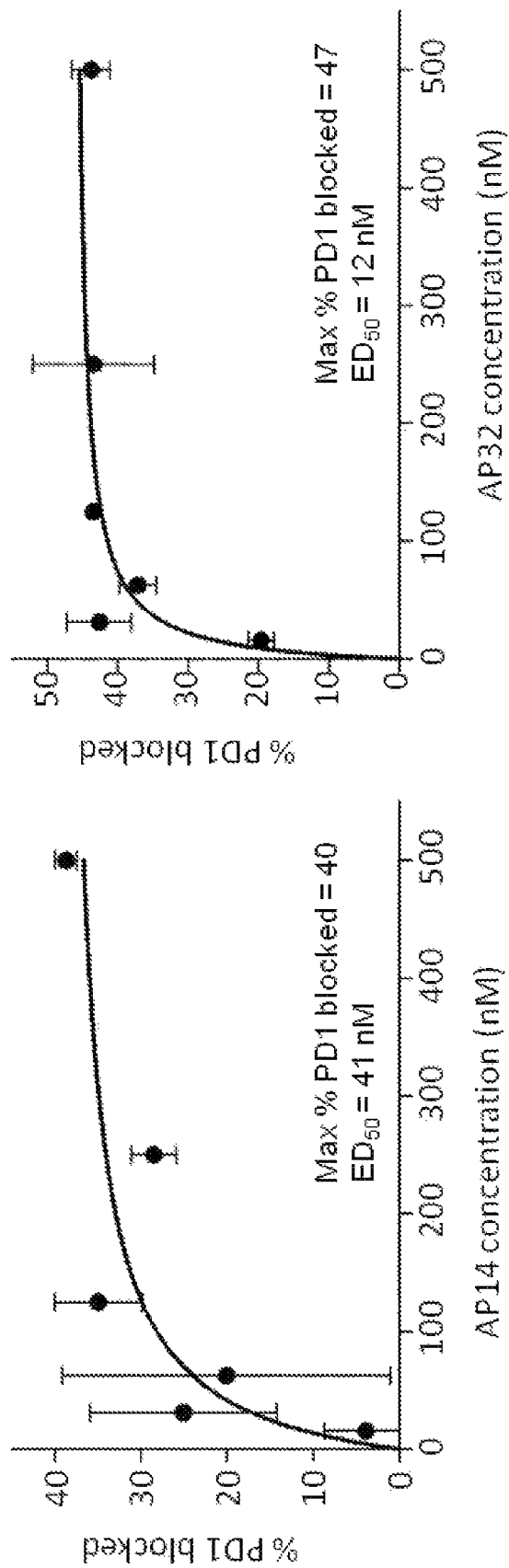
FIG. 4 includes charts showing the 50% effective dose ($ED_{50}$) of AP14 (left panel) and AP32 (right panel) as PDL1 antagonistic aptamers. The $ED_{50}$ for AP14 is 41 nM (left panel). The $ED_{50}$ for AP32 is 12 nM (right panel).

To further investigate 50% effective dose of AP14 and AP32 as PDL1 blocking agents, serial diluted AP14 and AP32 ranged from 12.5 nmole/l to 500 nmole/l were used in previously mentioned ELISA-based competition assay. The 50% effective dose was calculated by GraphPad Prism 5 using the equation $Y=B_{max} \times X/(ED50+X)$. $B_{max}$ is the maximum percentage of human PD1 protein which blocked by PDL1 antagonistic aptamer. The ED50 of AP14 and AP32 were 41 nmole/l and 12 nmole/l, respectively (FIG. 4).

Figure 6:
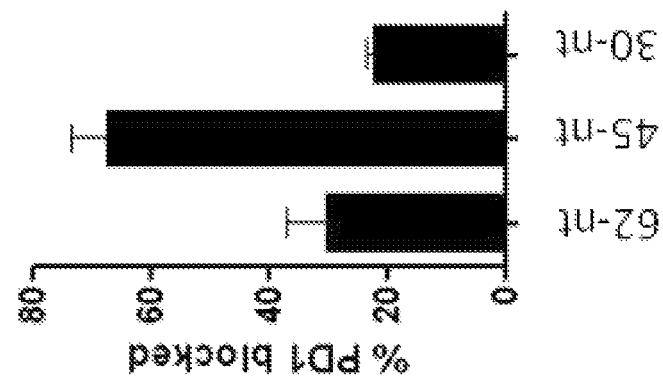
FIG. 6 is a graph showing the efficacy of anti-PDL1 aptamers (62-nt, 45-nt and 30-nt of FIG. 5) for blocking the PD-1:PDL1 interaction, using a competition assay.

In order to find the minimal sequences of AP32 required for PDL1 binding, truncations of aptamer sequences relating to AP32 were generated. According the predicted structure from Mfold, sequences at 5' and 3' ends of AP32 formed a long stem and the remaining sequences formed two short stem loops (FIG. 5, left panel). Two truncated aptamers related to AP32 aptamers, 45-nucleotides long (FIG. 5, middle panel) and 30-nucleotides long (FIG. 5, middle panel) were designed and their antagonistic function were examined by the previously mentioned ELISA-based competition assay. 45-nucleotides long truncated aptamer showed increased antagonistic function compared to 62-nucleotides long aptamer (65% and 35% respectively) (FIG. 6). However, with further sequence truncation, 30-nucleotides long truncated aptamer showed decreased blocking ability against the PD-1:PDL1 interaction. This 45-nucleotide long truncated AP32 aptamer was denoted as aptPDL1 hereafter.

EXAMPLE 4

Figure 7:
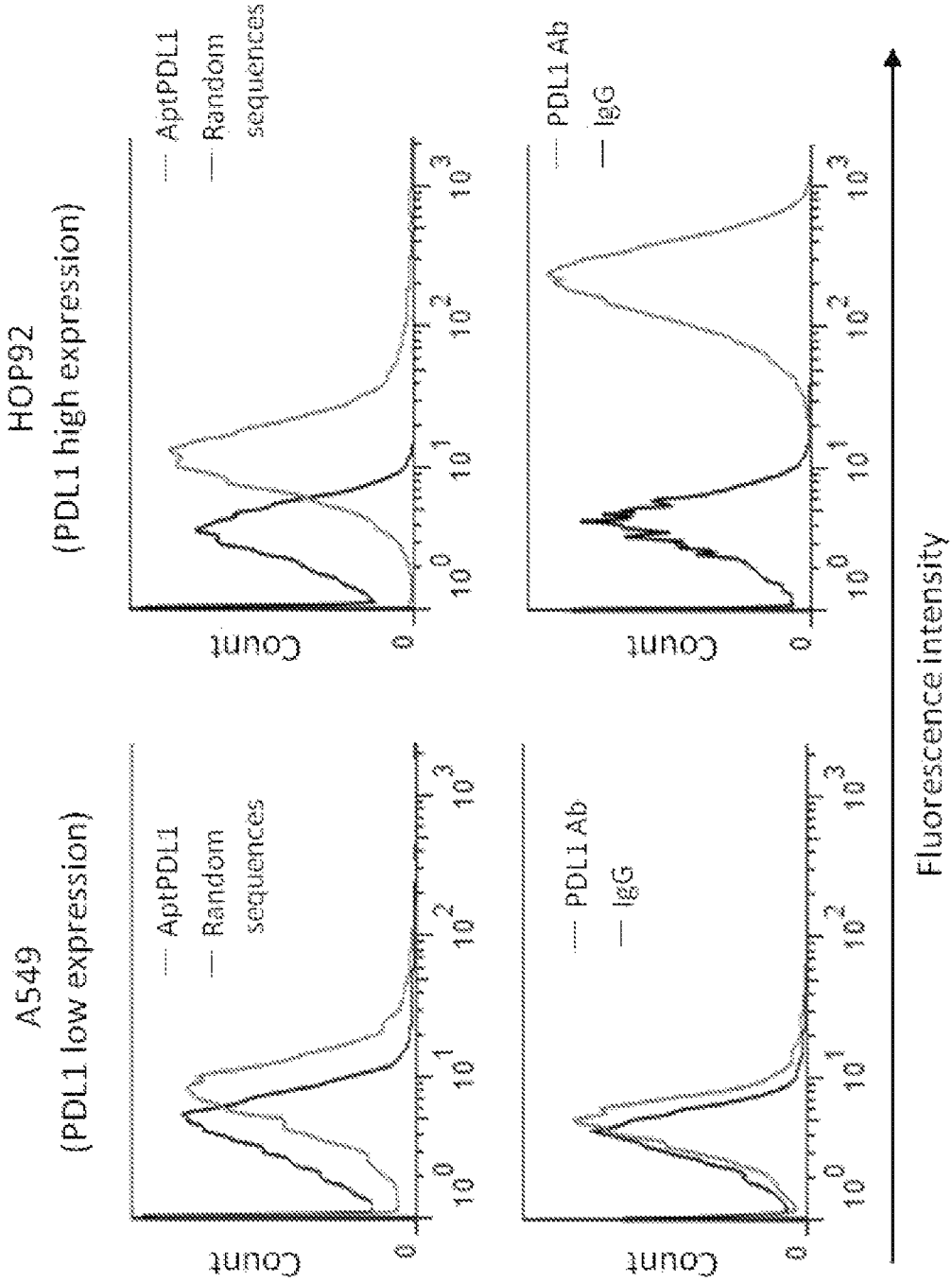
FIG. 7 includes graphical representations of data showing the binding ability of AptPDL1 to A549 (top left panel) and HOP92 (top right panel) human cancer cells that exhibit high and low PDL1 expression levels, respectively. As a control, the binding ability of an anti-PDL1 antibody to A549 (bottom left panel) and HOP92 (bottom right panel) human cancer cells is shown.

Investigate the Binding Ability of PDL1 Aptamer to Human and Mouse Cancer Cells Through Flow Cytometry Analysis To investigate the binding ability of aptPDL1 to PDL1-expressing cells, two human cancer cells with different PDL1 expression level were used. Fluorescence-labeled aptPDL1 (100 nmole/l) was incubated with A549 (PDL1 low expression) and HOP92 (PDL1 high expression) respectively and fluorescence intensity emitted from cells was detected by flow cytometry. Random sequences labeled with fluorescent dye were used as negative control. Consistent with PDL1 expression, stronger fluorescence intensity was detected from PDL1 highly expressing cell HOP92, while weaker signal was detected from A549 with lower PDL1 expression (FIG. 7).

Figure 8:
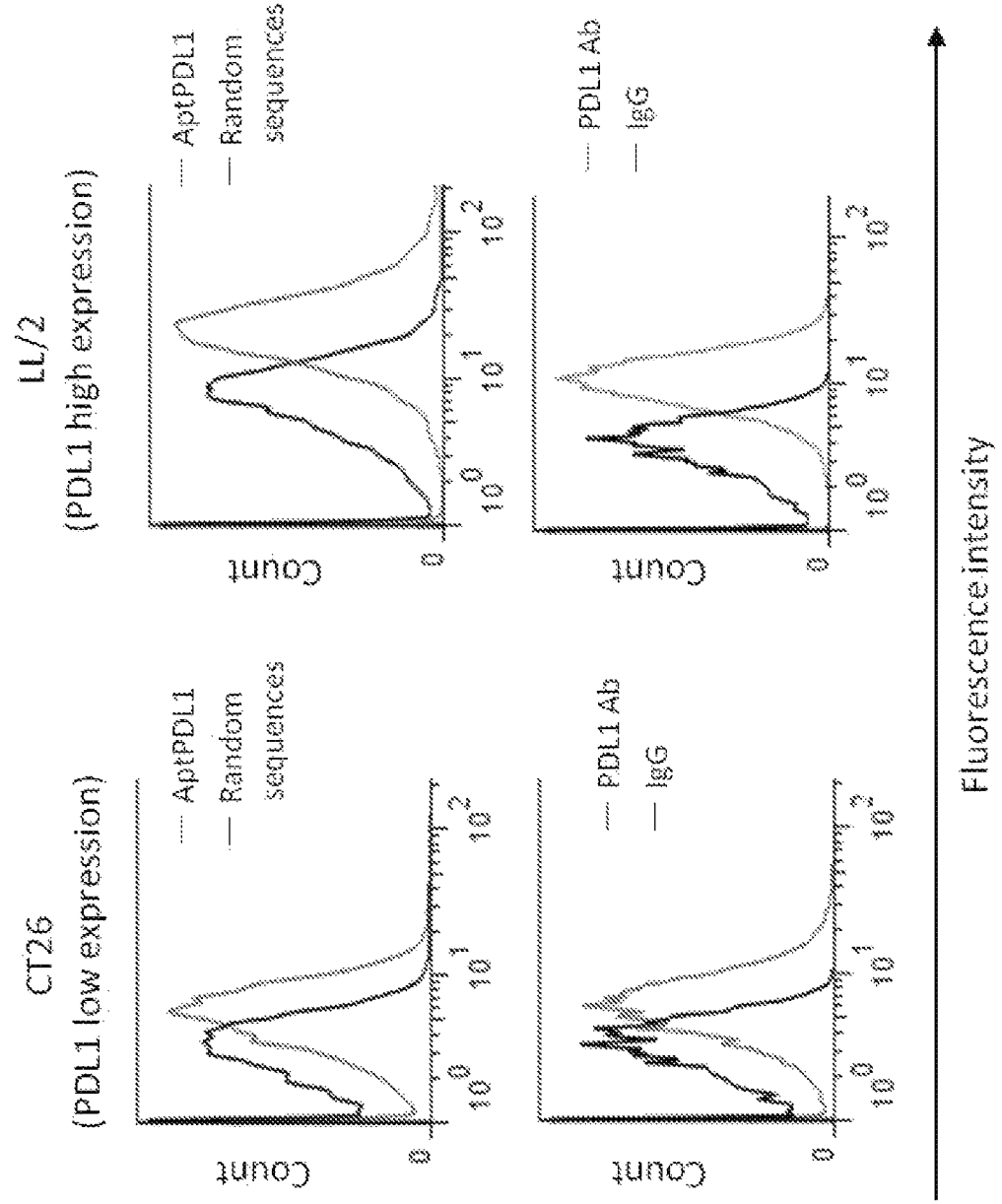
FIG. 8 includes graphical representations of data showing the binding ability of AptPDL1 to CT26 (top left panel) and LL/2 (top right panel) mouse cancer cells that exhibit high and low PDL1 expression levels, respectively. As a control, the binding ability of an anti-PDL1 antibody to CT26 (bottom left panel) and LL/2 (bottom right panel) mouse cancer cells is shown.
Figure 9:
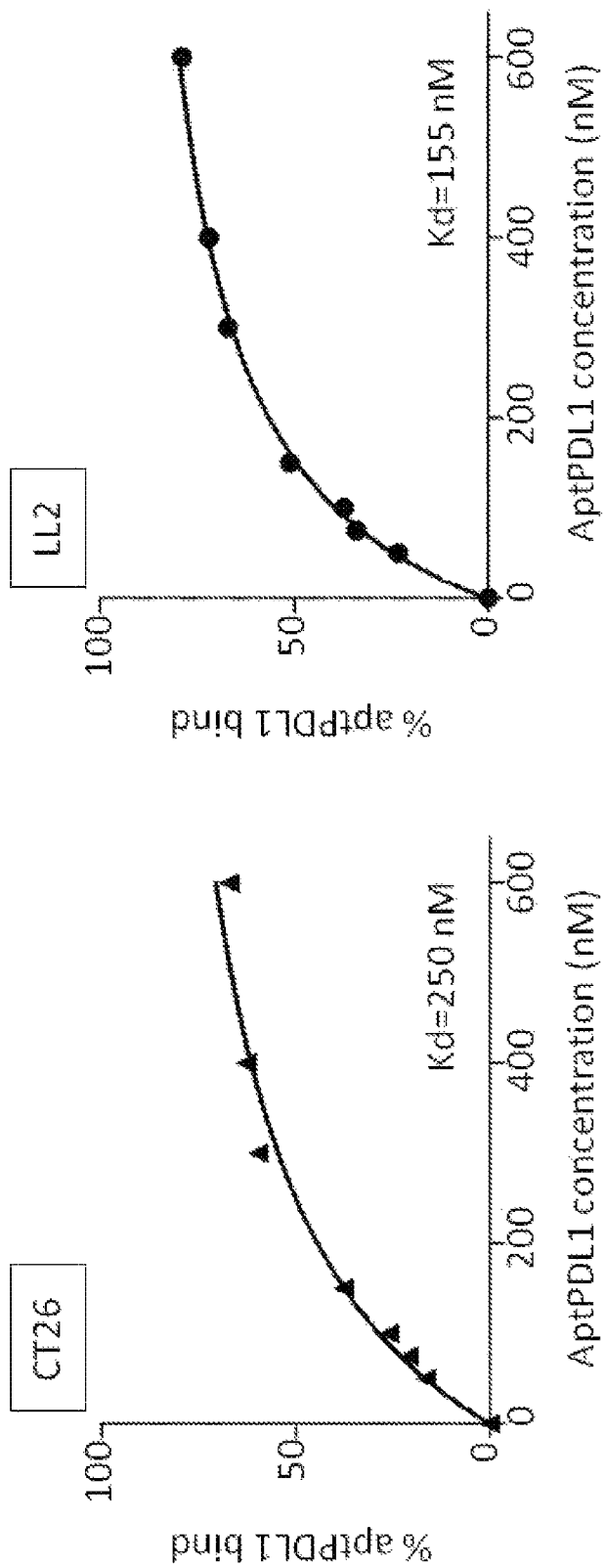
FIG. 9 includes graphical representations of data showing the dissociation constant of aptPDL1 to CT26 (left panel) and LL2 (right panel) mouse cancer cells.

The binding ability of aptPDL1 to mouse PDL1-expressing cells was evaluated using CT26 and LL/2 mouse cancer cells (FIG. 8). AptPDL1 could bind to both CT26 and LL/2

EXAMPLE 5

Figure 10:
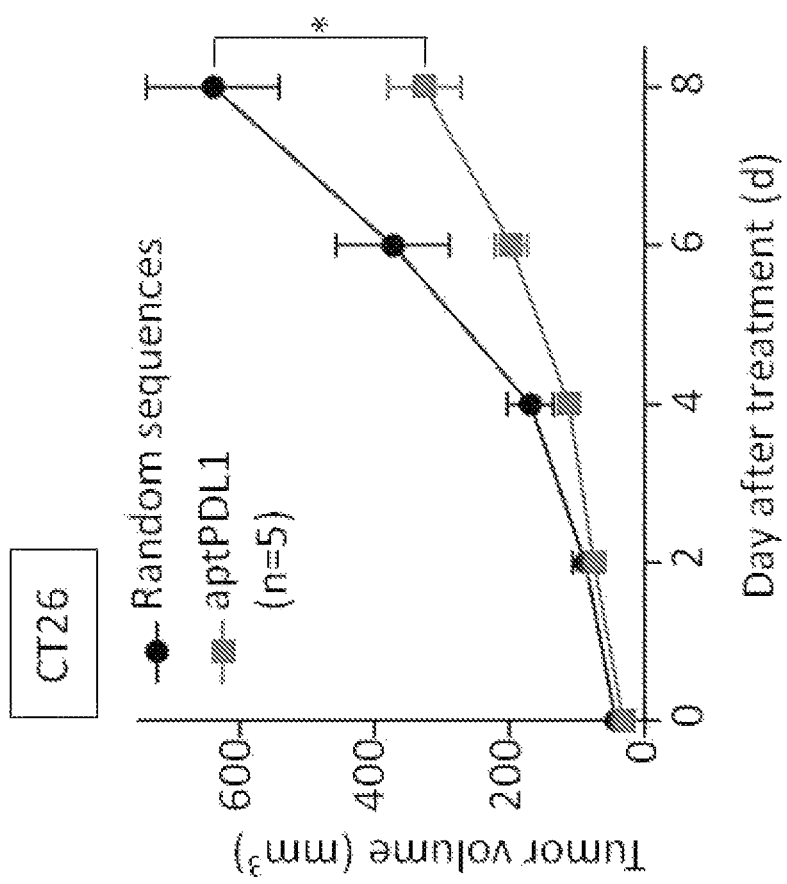
FIG. 10 is a graph showing the suppression effect of aptPDL1 on CT26 colorectal cancer cells in vivo using a syngeneic mouse model. The data show an approximate 50% suppression in tumor growth when mice are treated with aptPDL1 that is administered through intratumoral injection.
Figure 11:
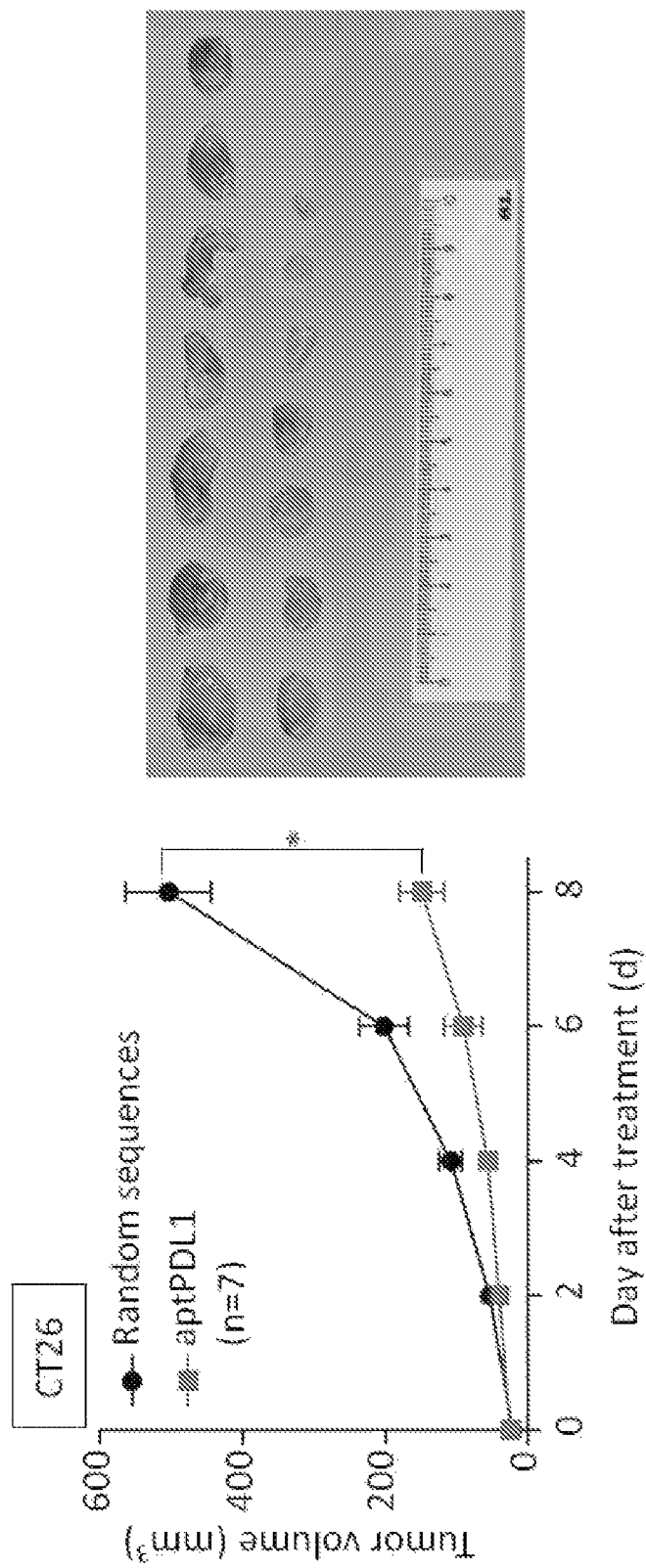
FIG. 11 is a graph showing the suppression effect of aptPDL1 on CT26 colorectal cancer cells in vivo using a syngeneic mouse model (left panel). The data show an approximate 73% suppression in tumor growth when mice are treated with aptPDL1 that is administered through intraperitoneal injection. Images of the tumors (right panel) from mice treated with aptPDL1 (bottom row of tumors) or control Random sequences (top row of tumors) are shown in the right panel.

Examine the Anti-Tumor Efficacy of PDL1 Antagonistic Aptamer in Syngeneic Animal Model To investigate the efficacy of PDL1 antagonistic aptamer as immunotherapy agents against cancer progression, syngeneic mice model was used. Balb/c mice were subcutaneously inoculated CT26 mouse colorectal cancer cells ($2\times10^5$ cells). When the tumor length reached 5 mm, drugs were administrated. For intratumoral injection group, 6 ug random sequences (n=5) or aptPDL1 (n=5) was intratumorally delivered every two days for total 4 times of injection. For intraperitoneal injection group, 30 ug random sequences (n=7) or aptPDL1 (n=7) was intraperitoneally delivered every two days for total 4 times of injection. AptPDL1 revealed significant inhibitory effect on tumor growth; 50% suppression in intratumorally injection group (FIG. 10) and 73% inhibition in intraperitoneal injection group (FIG. 11).

EXAMPLE 6

Figure 12:
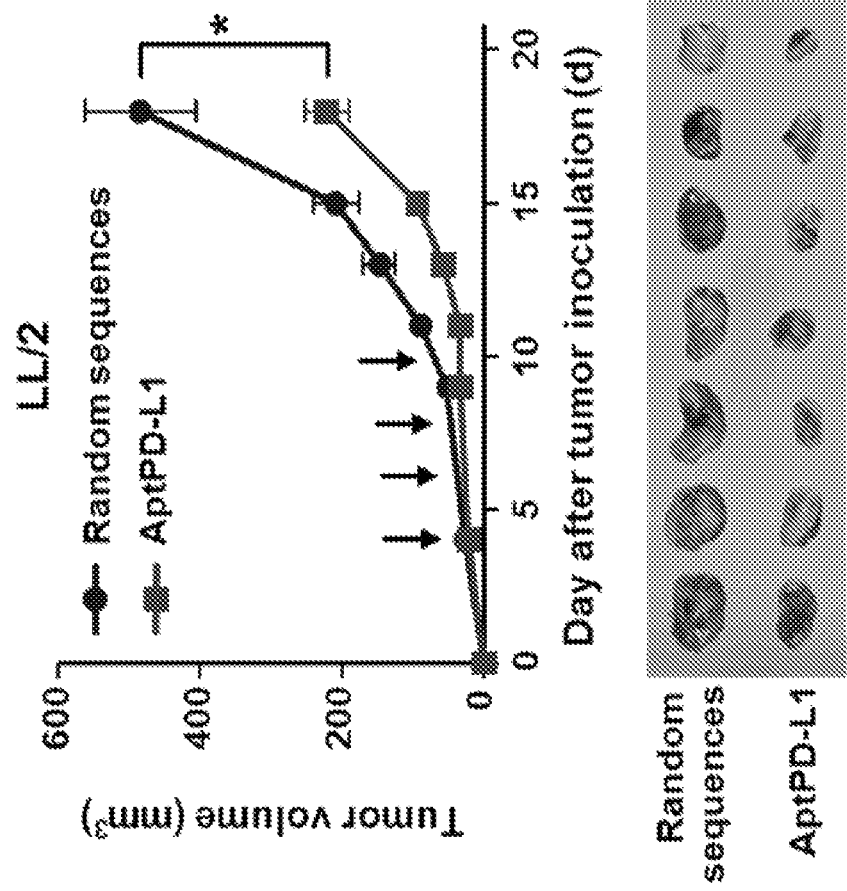
FIG. 12 is a graph showing the suppression effect of aptPDL1 on LL/2 lung carcinoma cells in vivo using a syngeneic mouse model (top). The data show that successive does of intraperitoneally aptPDL1 administration led to significant tumor-suppressive effect in LL/2-inoculated mice. Images of the tumors (bottom panel) from mice treated with aptPDL1 (bottom row of tumors) or control Random sequences (top row of tumors) are shown in the bottom panel.
Figure 13:
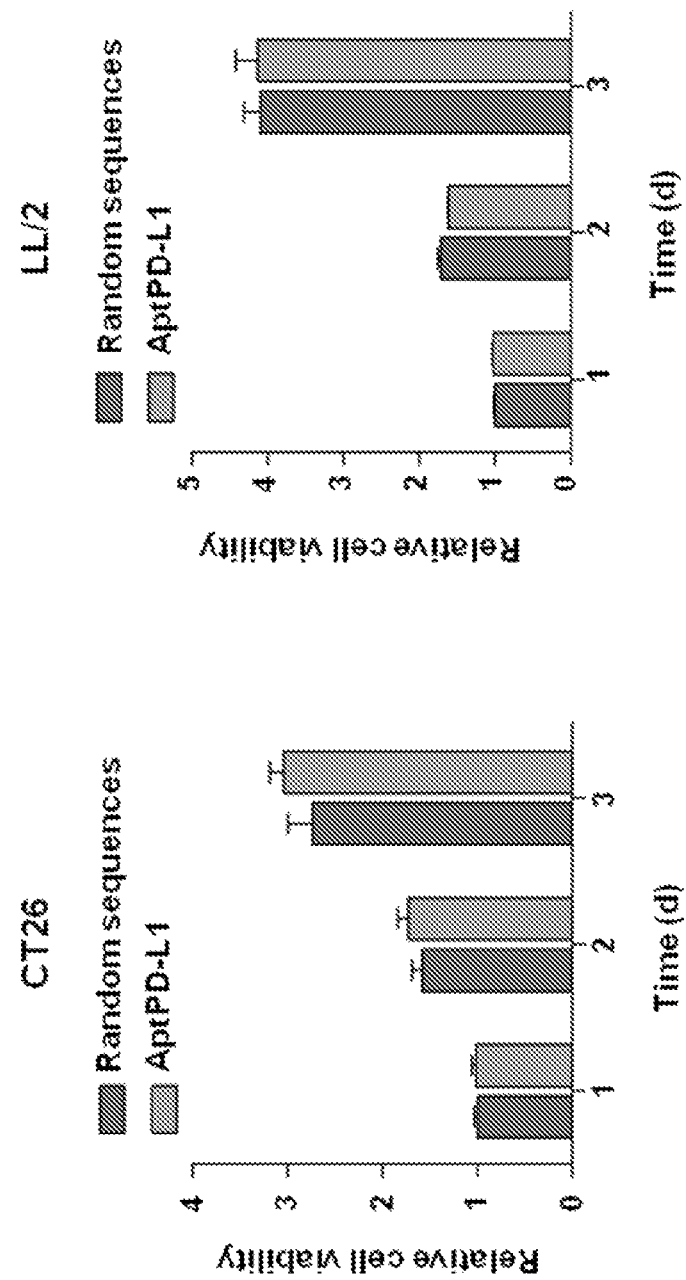
FIG. 13 is a graph showing the cytotoxicity of aptPDL1 against CT26 (left panel) and LL/2 (right panel) cells using in vitro cell viability assays. The data show that aptPDL1 has no direct cytotoxicity on CT26 (left) and LL/2 (right) cancer cells.

Examine the Anti-Tumor Efficacy of PDL1 Antagonistic Aptamer in Syngeneic Animal Model LL/2 murine syngeneic tumor models were adopted in the study of aptPDL1 in vivo tumor inhibitory function. C57BL/6 mice were inoculated subcutaneously with LL/2 ($1\times10^5$ cells). When the long-axis of tumors reached ~5 mm, 30 μg random-sequence oligonucleotides (n=7) or aptPDL1 (n=7) was administrated intraperitoneally every 2 days. The data showed that successive doses of intraperitoneally aptPDL1 administration led to significant tumor-suppressive effect in LL/2-inoculated C57BL/6 mice (FIG. 12). To exclude direct cytotoxicity of aptPDL1 against CT26 and LL/2 cells, we performed in vitro cell viability assays. CT26 or LL/2 cells ($2\times10^3$ cells) were seeded into wells of a 96-well plate, and random-sequence oligonucleotides or aptPDL1 (1 μM) was added into each well. After 24, 48, or 72 h, cell viability was assay using MTT (3-[4,5-dimethyl-thiazol-2-yl]-2,5-diphenyltetrazolium bromide) assays following standard procedures. These experiments showed that aptPDL1 has no direct cytotoxicity on cancer cells (FIG. 13).

EXAMPLE 7

Examine the Cytokine Expression in PDL1 Antagonistic Aptamer-Treated Tumor Tissues Analyses of responders to Atezolizumab (Roche), an anti-PDL1 antibody, revealed increased IFNγ and chemokine CXCL9/10 levels in the post-treatment tumors. We therefore examined whether similar phenomena were observed in the aptPDL1-treated CT26 and LL/2 tumors. RNA, extracted from tissues dissected from mice, was purified using a conventional TRIzol (Invitrogen) method following the manufacturer's protocol. cDNA was synthesized from total RNA using oligo(dT)$_{12-18}$ primers and SuperScript III reverse transcriptase (Invitrogen). qPCR was performed on a LightCycler 480 system (Roche Applied Science, Mannheim, Germany) using cDNA as a template and the following primer pairs (Integrated DNA Technologies): IFNγ, 5'-GAGGAACTGGCAAAAGGATG-3' (forward; SEQ ID NO: 18) and 5'-TTCAAGACT-TCAAAGAGTCTGAGGTA-3' (reverse; SEQ ID NO: 19); CXCL9, 5'-CTTTTCCTCTTGGGCATCAT-3' (forward; SEQ ID NO: 20) and 5'-GCATCGTGCATTCCTTATCA-3' (reverse; SEQ ID NO: 21); CXCL10, 5'-GCTGCCGT-CATTTTCTGC-3' (forward; SEQ ID NO: 22) and 5'-TCT-CACTGGCCCGTCATC-3' (reverse; SEQ ID NO: 23); CXCL11, 5'-GCTGCTGAGATGAACAGGAA-3' (forward; SEQ ID NO: 24) and 5'-CCCTGTTT-GAACATAAGGAAGC-3' (reverse; SEQ ID NO: 25); and β-actin, 5'-CTAAGGCCAACCGTGAAAAG-3' (forward; SEQ ID NO: 26) and 5'-ACCAGAGGCATACAGGGACA-3' (reverse; SEQ ID NO: 27). Protein was extracted from tumor tissue using RIM buffer supplemented with protease inhibitor cocktail (Roche Applied Science). Primary antibodies against the murine proteins CXCL9, CXCL10, and CXCL11 (R&D Systems, Minneapolis, Minn., USA) were used at a 1:500 dilution. The primary antibody against β-actin (Santa Cruz Biotechnology, Santa Cruz, Calif., USA) was used at 1:10000 dilution. HRP-labeled secondary antibodies were used at a 1:5000 dilution (Santa Cruz Biotechnology).

Figure 14:
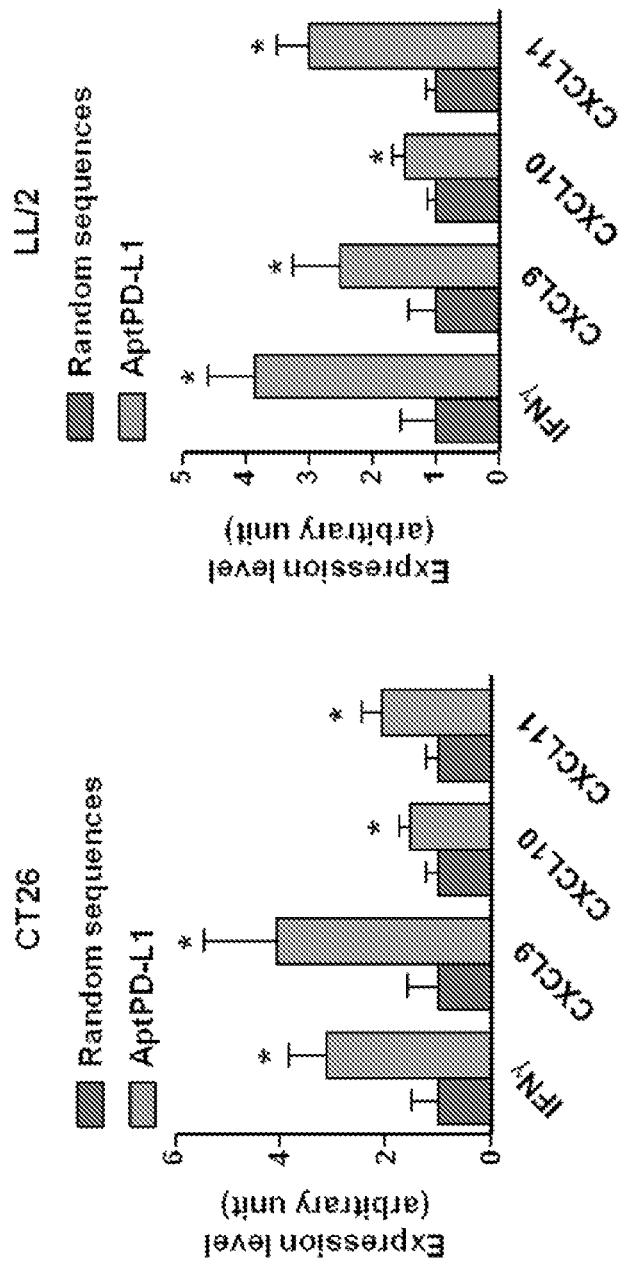
FIG. 14 is a graph showing the expression levels of IFNγ and chemokine CXCL9/10/11 in aptPDL1-treated CT26 (left panel) and LL/2 (right panel) tumors. Expression levels of IFNγ and chemokine CXCL9/10/11 were determined using RNA extracted from tissue and quantified by reverse-transcription quantitative PCR. The data show elevated levels of IFNγ, CXCL9, CXCL10, and CXCL11 in aptPDL1-treated CT26 (left) and LL/2 (right) tumors.
Figure 15:
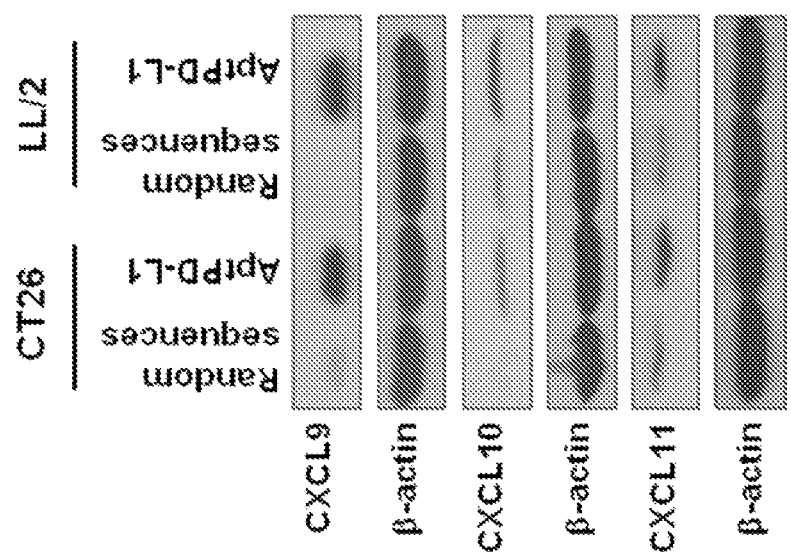
FIG. 15 is an immunoblot showing the expression levels of chemokine CXCL9/10/11 in aptPDL1-treated CT26 and LL/2 tumors. Expression levels of chemokine CXCL9/10/11 were determined using protein extracted from tissue and protein-specific antibodies. Analysis of β-actin levels was performed as a control. The data show elevated levels of CXCL9, CXCL10, and CXCL11 in aptPDL1-treated CT26 (left) and LL/2 (right) tumors.

Consistent with these previous findings, both reverse-transcription quantitative PCR and immunoblot analyses showed elevated IFNγ, CXCL9, CXCL10, and CXCL11 levels in aptPDL1-treated tumors (FIGS. 14 and 15).

EXAMPLE 8

Figure 16:
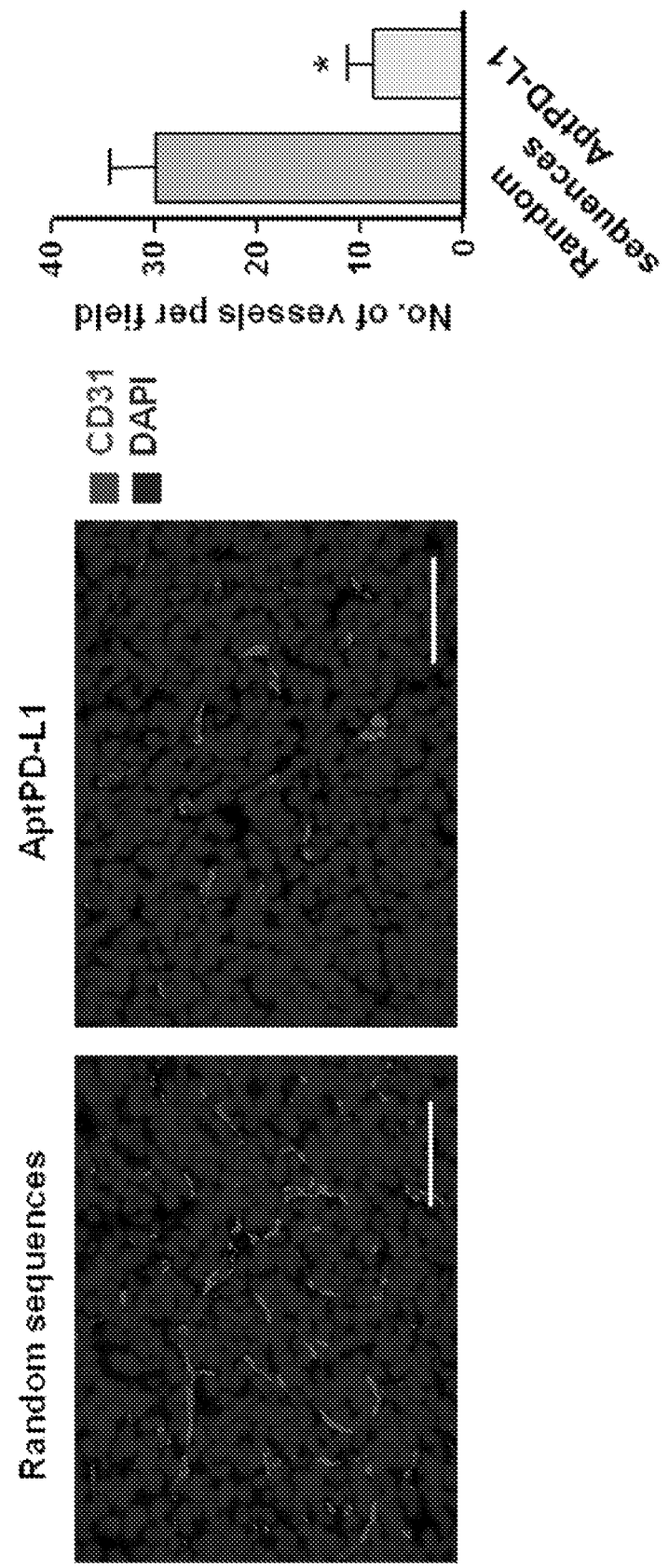
FIG. 16 includes diagrams showing fluorescent images of CD31-positive intratumoral microvessels in control and aptPDL1 treated tumors and a graph of intratumoral microvessels density quantification. A: photos showing fluorescent image signals of CD31-posotive intratumoral microvessels in mice treated with a control aptamer (left) and aptPDL1 (right). B: A chart quantitating the fluorescent image signals shown in panel A. The data show both the length and density of CD31-positive intratumoral microvessels were significantly decreased in the aptPDL1 treatment group.

Examine the Microvessel Formation in PDL1 Antagonistic Aptamer-Treated Tumor Tissues Intratumoral CXCL9/10 have been reported to exert anti-tumor effects. The chemokines CXCL9/10/11 are also known to inhibit angiogenesis through their binding to endothelial chemokine (C—X—C motif) receptor 3 (CXCR3). Therefore, we investigated the effects of aptPDL1 treatment on intratumoral microvessels. Formalin-fixed, paraffin-embedded tissues were rehydrated and subjected to an antigen-retrieval process in citrate buffer (pH 6.0). Primary antibodies against CD31 (Abcam) were used at a 1:100 dilution. Alexa Fluor 647-labeled secondary antibodies (Abcam) were used at a 1:500 dilution. Nuclei were stained with DAPI in Fluoroshield mounting medium (Abcam). As shown in FIG. 16, both the length and density of CD31-positive intratumoral microvessels were significantly decreased in the aptPDL1 treatment group.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A nucleic acid aptamer capable of binding programmed death-ligand protein 1 (PDL1), wherein the aptamer comprises a nucleic acid motif having the nucleotide sequence of 5'-CGGGCCACAT-3' (SEQ ID NO:1), and wherein the nucleic acid aptamer comprises a nucleic acid sequence that is at least 85% identical to (SEQ ID NO: 2)
ACGGGCCACATCAACTCATTGATAGACAATGCGTCCACTGCCCGT.

2. The nucleic acid aptamer of claim 1, wherein the nucleic acid aptamer is about 30-62 nucleotide (nt) in length.

3. The nucleic acid aptamer of claim 1, wherein the nucleic acid aptamer comprises a nucleic acid sequence that is at least 90% identical to SEQ ID NO: 2.

4. The nucleic acid aptamer of claim 1, wherein the nucleic acid aptamer comprises a nucleic acid sequence that is at least 95% identical to SEQ ID NO: 2.

5. The nucleic acid aptamer of claim 1, wherein the nucleic acid aptamer comprises the nucleic acid sequence of SEQ ID NO:2.

6. The nucleic acid aptamer of claim 5, wherein the nucleic acid aptamer consists of the nucleotide acid sequence of SEQ ID NO:2.

7. A nucleic acid aptamer capable of binding programmed death-ligand protein 1 (PDL1), wherein the aptamer comprises a nucleic acid sequence that is at least 85% identical to:

(i)
(SEQ ID NO: 2)
ACGGGCCACATCAACTCATTGATAGACAATGCGTCCACTGCCCGT;

(ii)
(SEQ ID NO: 3)
CACTCAATAATTCCACTGCTACATACGTTT;

(iii)
(SEQ ID NO: 4)
AAACTAGGGTCCATTTGTGTACCTGCGA;

(iv)
(SEQ ID NO: 5)
ACATCAACTTGATAGACAACTGCGTCCACT;

-continued (v)
(SEQ ID NO: 6)
CATCTGGTACCTTACGACGCTTCATCTCCC;

(vi)
(SEQ ID NO: 7)
CATGTTTTCGAAAGACAATCCGCTGCCCTG;
or (vii)
(SEQ ID NO: 8)
CATGTTCCTTTCGTTCTGCCTTTTCCTTCC.

8. The nucleic acid aptamer of claim 7, wherein the aptamer comprises a nucleic acid sequence that is at least 90% identical to (i)
(SEQ ID NO: 2)
ACGGGCCACATCAACTCATTGATAGACAATGCGTCCACTGCCCGT;

(ii)
(SEQ ID NO: 3)
CACTCAATAATTCCACTGCTACATACGTTT;

(iii)
(SEQ ID NO: 4)
AAACTAGGGTCCATTTGTGTACCTGCGA;

(iv)
(SEQ ID NO: 5)
ACATCAACTTGATAGACAACTGCGTCCACT;

(v)
(SEQ ID NO: 6)
CATCTGGTACCTTACGACGCTTCATCTCCC;

(vi)
(SEQ ID NO: 7)
CATGTTTTCGAAAGACAATCCGCTGCCCTG;
or (vii)
(SEQ ID NO: 8)
CATGTTCCTTTCGTTCTGCCTTTTCCTTCC.

9. The nucleic acid aptamer of claim 8, wherein the aptamer comprises a nucleic acid sequence that is at least 95% identical to (i)
(SEQ ID NO: 2)
ACGGGCCACATCAACTCATTGATAGACAATGCGTCCACTGCCCGT;

(ii)
(SEQ ID NO: 3)
CACTCAATAATTCCACTGCTACATACGTTT;

(iii)
(SEQ ID NO: 4)
AAACTAGGGTCCATTTGTGTACCTGCGA;

(iv)
(SEQ ID NO: 5)
ACATCAACTTGATAGACAACTGCGTCCACT;

(v)
(SEQ ID NO: 6)
CATCTGGTACCTTACGACGCTTCATCTCCC;

(vi)
(SEQ ID NO: 7)
CATGTTTTCGAAAGACAATCCGCTGCCCTG;
or (vii)
(SEQ ID NO: 8)
CATGTTCCTTTCGTTCTGCCTTTTCCTTCC.

10. The nucleic acid aptamer of claim 9, wherein the aptamer comprises a nucleic acid sequence of (i)
(SEQ ID NO: 2)
ACGGGCCACATCAACTCATTGATAGACAATGCGTCCACTGCCCGT;

(ii)
(SEQ ID NO: 3)
CACTCAATAATTCCACTGCTACATACGTTT;

(iii)
(SEQ ID NO: 4)
AAACTAGGGTCCATTTGTGTACCTGCGA;

(iv)
(SEQ ID NO: 5)
ACATCAACTTGATAGACAACTGCGTCCACT;

(v)
(SEQ ID NO: 6)
CATCTGGTACCTTACGACGCTTCATCTCCC;

(vi)
(SEQ ID NO: 7)
CATGTTTTCGAAAGACAATCCGCTGCCCTG;
or (vii)
(SEQ ID NO: 8)
CATGTTCCTTTCGTTCTGCCTTTTCCTTCC.

11. The nucleic acid aptamer of claim 7, wherein the nucleic acid aptamer is about 30-62 nucleotide (nt) in length.

12. A pharmaceutical composition, comprising (i) the nucleic acid aptamer of claim 1; and (ii) a pharmaceutically acceptable carrier.

13. A pharmaceutical composition, comprising (i) the nucleic acid aptamer of claim 10; and (ii) a pharmaceutically acceptable carrier.

14. A method for treating cancer, comprising administering to a subject in need thereof an effective amount of the pharmaceutical composition of claim 12.

15. The method of claim 14, wherein the subject is a human patient having, suspected of having, or at risk for cancer.

16. The method of claim 14, wherein the cancer is melanoma, non-small cell lung cancer, colorectal cancer, or renal-cell cancer.

17. A method of enhancing immune activity in a subject, the method comprising administering to a subject in need thereof an effective amount of the pharmaceutical composition of claim 12.

18. The method of claim 17, wherein the subject is a human patient having, suspected of having, or at risk for cancer.

19. The method of claim 18, wherein the cancer is melanoma, non-small cell lung cancer, colorectal cancer, or renal-cell cancer.

20. The method of claim 17, wherein the subject is a human patient having or suspected of having an infectious disease.

21. The method of claim 20, wherein the infectious disease is caused by enterovirus, hepatitis B virus (HBV), hepatitis C virus (HCV), hepatitis A virus (HAV), hepatitis D virus (HDV) or hepatitis E virus (HEV).

22. The method of claim 17, wherein the amount of the pharmaceutical composition is effective in increasing activation of one or more of T cells, B cells, dendritic cells, natural killer cells, or macrophages.

23. The method of claim 17, wherein the amount of the pharmaceutical composition is effective in increasing the proliferation of CD8 positive T cells.

* * * * *